United States Patent
Claessens et al.

(10) Patent No.: US 11,751,952 B2
(45) Date of Patent: Sep. 12, 2023

(54) REDUCING SENSOR INTERFERENCE IN A MEDICAL DEVICE

(71) Applicant: KONINKLIJKE PHILIPS N.V., Eindhoven (NL)

(72) Inventors: Eric Franciscus Johannes Claessens, Helmond (NL); Jan Harm De Boer, Nuenen (NL); Patrick Wilhelmus Van Kaam, Best (NL); Ioannis Pappous, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 202 days.

(21) Appl. No.: 17/265,635

(22) PCT Filed: Jul. 29, 2019

(86) PCT No.: PCT/EP2019/070296
§ 371 (c)(1),
(2) Date: Feb. 3, 2021

(87) PCT Pub. No.: WO2020/030453
PCT Pub. Date: Feb. 13, 2020

(65) Prior Publication Data
US 2021/0298840 A1    Sep. 30, 2021

Related U.S. Application Data

(60) Provisional application No. 62/716,154, filed on Aug. 8, 2018.

(30) Foreign Application Priority Data

Oct. 5, 2018  (EP) ........................................ 8198776

(51) Int. Cl.
  *A61B 34/20*    (2016.01)
  *A61B 8/08*     (2006.01)
  *A61B 8/00*     (2006.01)

(52) U.S. Cl.
  CPC ............ *A61B 34/20* (2016.02); *A61B 8/0841* (2013.01); *A61B 8/4245* (2013.01); *A61B 8/463* (2013.01);
  (Continued)

(58) Field of Classification Search
  CPC .................. A61B 34/20; A61B 8/0841; A61B 2034/2063
  See application file for complete search history.

(56) References Cited

U.S. PATENT DOCUMENTS

2003/0048698 A1    3/2003  Barnes
2007/0268272 A1   11/2007  Perski
                  (Continued)

FOREIGN PATENT DOCUMENTS

WO    2007047966 A2    4/2007
WO    2015155671 A1   10/2015
                  (Continued)

OTHER PUBLICATIONS

International Search Report and Written Opinion of PCT/EP2019/070296, dated Oct. 9, 2019.
(Continued)

*Primary Examiner* — Dixomara Vargas

(57) ABSTRACT

A medical sensing system (100) includes an elongate interventional device (101) and an adjustable capacitance circuit (102). The elongate interventional device (101) includes a sensor (103) having a capacitance ($C_{ss}$). The elongate interventional device (101) also includes a first electrical conductor (104) and a second electrical conductor (105). The first electrical conductor (104) and the second electrical
(Continued)

conductor (105) are in electrical contact with the sensor (103) and extend along the elongate interventional device (101). The elongate interventional device (101) also includes i) an electrically conductive shield (106) that overlaps the electrical conductors (104, 105) and/or ii) an electrically conductive shaft (107). The adjustable capacitance circuit (102) provides an adjustable capacitance ($C_{Adj}1$, $C_{Adj}2$) between at least one of the electrical conductors (104, 105) and i) the electrically conductive shield (106) that overlaps the electrical conductors (104, 105) and/or ii) the electrically conductive shaft (107).

18 Claims, 5 Drawing Sheets

(52) U.S. Cl.
CPC .... *A61B 8/5207* (2013.01); *A61B 2034/2063* (2016.02)

(56) References Cited

U.S. PATENT DOCUMENTS

| 2012/0158077 A1* | 6/2012 | Buessing | A61N 1/056 607/8 |
| 2013/0245741 A1* | 9/2013 | Atalar | A61N 1/06 607/148 |
| 2014/0018668 A1 | 1/2014 | Zheng | |

FOREIGN PATENT DOCUMENTS

| WO | 2017167594 A1 | 10/2017 | |
| WO | 2018095793 A1 | 5/2018 | |
| WO | WO-2018095793 A1 * | 5/2018 | ......... A61B 17/3403 |

OTHER PUBLICATIONS

Mung, Jay et al "A Non-Disruptive Technology for Robust 3D Tool Tracking for Ultrasound-Guided Interventions", MICCAI 2011, Part 1, LNCS 6891, pp. 153-160. Abstact Only.

* cited by examiner

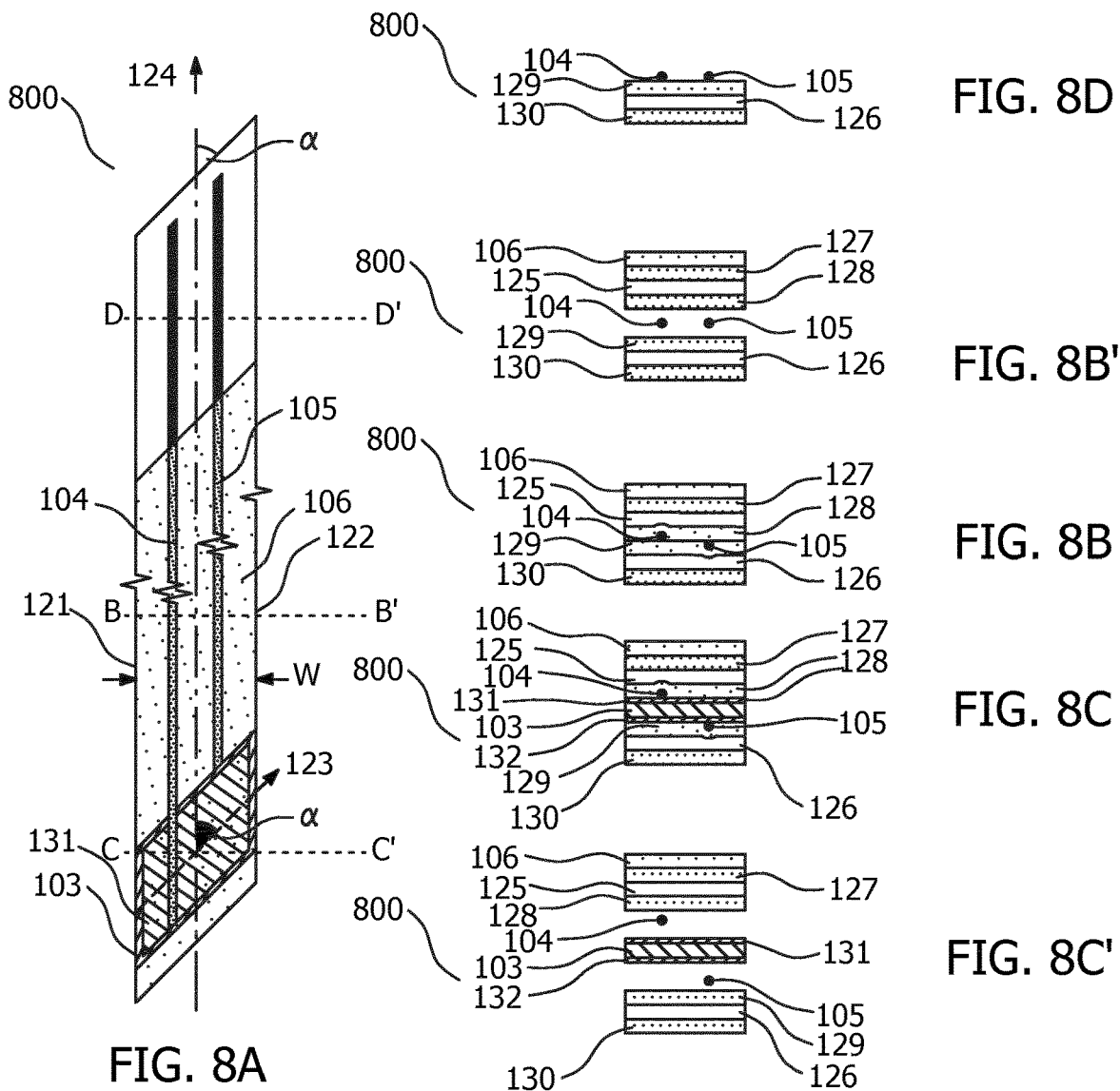
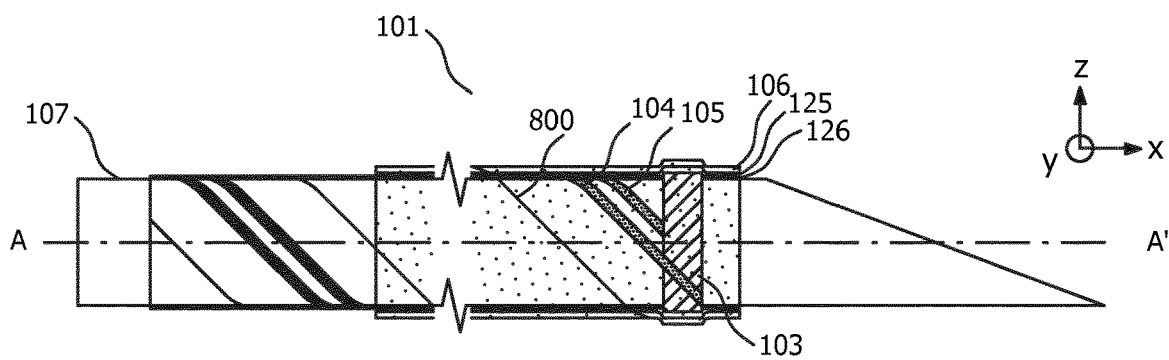

REDUCING SENSOR INTERFERENCE IN A MEDICAL DEVICE

CROSS-REFERENCE TO PRIOR APPLICATIONS

This application is the U.S. National Phase application under 35 U.S.C. §§ 371 of International Application No. PCT/EP2019/070296, filed on Jul. 29, 2019, which claims the benefit of U.S. Provisional Patent Application Ser. No. 62/716,154, filed Aug. 8, 2018 and European Patent Application No. 18198776.9, filed on Oct. 5, 2018. These applications are hereby incorporated by reference herein.

FIELD OF THE INVENTION

The invention relates to reducing interference to a sensor disposed on an interventional device. The use of a wide range of sensors on a wide range of interventional devices is contemplated, including an ultrasound sensor on a medical needle. The interventional device may be used in the medical field in general. In one exemplary application an ultrasound sensor on a medical needle may be used to track a position of the medical needle respective the ultrasound field of a beamforming ultrasound imaging probe.

BACKGROUND OF THE INVENTION

Interventional devices in the medical field increasingly incorporate sensors to gain more information about their surroundings within a patient's anatomy. Sensors of pressure, temperature, fluid flow, optical radiation, sound, and ultrasound that convert a physical parameter into an electrical signal, or electrodes that detect electrical signals may for example be incorporated in this regard. In one exemplary application described in more detail in document [1] "A Non-disruptive Technology for Robust 3D Tool Tracking for Ultrasound-Guided Interventions" by Jay Mung, Francois Vignon, and Ameet Jain, in MICCAI 2011, Part I, LNCS 6891, pp. 153-160, 2011, A. Martel, and T. Peters (Eds.), an ultrasound sensor is attached to a medical needle and used to track the position of the needle respective the ultrasound field of a beamforming ultrasound imaging probe.

One issue faced with such interventional devices is the need to reduce interference to the electrical signals generated by such sensors. Without appropriate measures, electromagnetic interference from nearby electrical devices can confound the analysis of signals from such sensors.

In this regard, various electrical shielding and grounding techniques are known. In one approach, document WO2015155671 discloses an interventional device in the form of a medical needle that has a piezoelectric polymer sensor attached thereto for use in a medical tracking application. Various interference-reducing techniques are discussed therein.

Another document WO 2007/047966 A2 discloses an MRI-safe high-impedance lead system. MRI/RF compatible medical interventional devices are disclosed. A plurality of spaced apart high impedance circuit segments are configured to have a high impedance at a high range of radiofrequencies and a low impedance at a low range of frequencies. The high impedance circuit segments may comprise co-wound coiled inductors and can reduce, block or inhibit RF transmission along the lead system during exposure to RF associated with a high-field magnet MRI systems, while permitting passage of low frequency physiologic signals, treatments and/or stimuli. The devices can include at least one electrode.

Another document US 2012/0158077 A1 relates to an implantable medical device that connects to function conductor(s) to transmit therapeutic signals or diagnostic signals or both. A controllable voltage/current source or adjustable terminating impedance for the function conductor and a control unit that is connected to the voltage or current source or adjustable terminating impedance. The control unit controls a voltage, or a current to be applied to the function line, or to adjust the terminating impedance. Includes an interference field sensor connected to the control unit, and to detect an alternating electromagnetic or magnetic field, and to supply an output signal, upon detection. The control unit controls the voltage/current source as a function of the output signal of the interference field sensor, or sets the adjustable impedance so that a voltage induced as the result of an alternating electromagnetic or magnetic field is compensated for at the distal end of the electrode line Despite this progress there remains room to reduce electromagnetic interference to electrical signals generated by a sensor disposed on an interventional device.

SUMMARY OF THE INVENTION

The invention seeks to reduce electromagnetic interference to electrical signals generated by a sensor disposed on an interventional device. Thereto, a medical sensing system is provided. The medical sensing system includes an elongate interventional device and an adjustable capacitance circuit. The elongate interventional device includes a sensor having a capacitance. The sensor is disposed on the elongate interventional device. A first electrical conductor and a second electrical conductor are in electrical contact with the sensor and extend along the elongate interventional device in order to provide electrical signals corresponding to signals detected by the sensor. The interventional device includes i) an electrically conductive shield that overlaps the electrical conductors and/or ii) an electrically conductive shaft. The first electrical conductor and the second electrical conductor each have a stray capacitance to the electrically conductive shield and/or to the electrically conductive shaft. The adjustable capacitance circuit provides an adjustable capacitance between at least one of the electrical conductors and i) the electrically conductive shield that overlaps the electrical conductors and/or ii) the electrically conductive shaft.

Sensors having a capacitance, i.e. capacitive sensors, typically operate by generating small amounts of charge in response to a change in a physical quantity, e.g. an ultrasound signal. The charge is then amplified in order to further process the physical signal. Such sensors may be susceptible to electromagnetic interference, i.e. EMI, which may confound the interpretation of electrical signals generated by such sensors, in particular hampering the determination of the change in physical quantity. EMI may be coupled to such sensors or to electrical wires that connect thereto. EMI may be coupled capacitively or inductively or by a combination of these mechanisms. The inventors have found that whilst conventional measures such as shielding the electrical sensor and/or the electrical wires may be used to reduce such EMI to a sensor disposed on an interventional device, these measures alone may still provide inadequate EMI reduction.

The present invention addresses a significant source of EMI that has its origins in differences in stray capacitance between i) an electrically conductive shield that overlaps the electrical conductors and/or ii) an electrically conductive shaft of the interventional device, and each of the electrical conductors that connect to the sensor. These differences in stray capacitance give rise to different amounts of EMI coupling to each of the electrical conductors that connect to the sensor, limiting the efficacy of common mode EMI reduction techniques such as differential amplification. These differences in stray capacitance have been found difficult to reduce to a negligible level through manufacturing process controls. The inventive adjustable capacitance circuit compensates for such differences by providing an adjustable capacitance between at least one of the electrical conductors and i) the electrically conductive shield that overlaps the electrical conductors and/or ii) the electrically conductive shaft. By adjusting the adjustable capacitance, more-similar amounts of interference may be coupled to each electrical conductor. The interference that is common to both electrical conductors, i.e. the common mode interference, may then be removed by e.g. differentially amplifying the signals on the electrical conductors. In so doing, a more sensitive sensor may be provided through a reduction in the EMI "interference floor".

According to one aspect the adjustable capacitance circuit includes at least one input that receives electrical signals indicative of interference signals detected on the first electrical conductor and/or on the second electrical conductor. The adjustable capacitance circuit controls the adjustable capacitance based on the detected interference signals. In so doing a reliable technique of reducing EMI is provided because it is based on the actual detected interference.

According to another aspect the adjustable capacitance circuit controls the adjustable capacitance based on a difference in stray capacitance measured between each electrical conductor and i) the electrically conductive shield that overlaps the electrical conductors and/or ii) the electrically conductive shaft. An alternative technique to the interference measurement technique is thus provided for reducing EMI.

According to another aspect the medical sensing system includes a differential amplifier. The differential amplifier is in electrical communication with each of the first electrical conductor and the second electrical conductor and provides an output signal corresponding to an amplified difference between an electrical signal on the first electrical conductor and an electrical signal on the second electrical conductor. The output signal may be used to control the input of the adjustable capacitance circuit and/or to provide a sensor signal. Since the output signal is a differential signal it is inherently indicative of the difference in interference signals on each of the two electrical conductors and thus may be used to adjust the adjustable capacitance in order to reduce EMI. When used to provide a sensor signal, the sensor signal advantageously has reduced EMI. Moreover the complexity of associated processing circuitry is reduced by using the same amplifier to provide both the sensor signal and the control signal for the adjustable capacitance circuit.

According to another aspect the elongate interventional device includes both i) an electrically conductive shield that overlaps the electrical conductors and ii) an electrically conductive shaft. The electrically conductive shield is electrically connected to the electrically conductive shaft. This connection reduces the complexity of the electrical shielding and provides for a more flexible interconnection between the medical sensing system and separate processing electronics since only a single electrical conductor is required to shield the electrical signals between the medical sensing system and separate processing circuitry.

In accordance with another aspect the sensor in the medical sensing system is an ultrasound sensor and the medical sensing system also includes a position determination unit that computes a position of the ultrasound sensor respective the ultrasound field of a beamforming ultrasound imaging probe.

Further aspects and their advantages are described with reference to the appended claims. Additional advantages of the invention to those described herein will also be apparent to the skilled person.

BRIEF DESCRIPTION OF THE FIGURES

FIG. 8 illustrates various views of a sensor strip 800 that includes sensor 103.

FIG. 9 illustrates an exemplary interventional device 101 that has sensor strip 800 wrapped around its shaft in the form of a spiral.

DETAILED DESCRIPTION OF THE INVENTION

In order to illustrate the principles of the present invention a medical sensing system is described with particular reference to an exemplary position tracking application in which an ultrasound sensor disposed on a medical needle is used to track a position of the interventional device respective the ultrasound field of a beamforming ultrasound imaging probe.

It is however to be appreciated that the invention finds application in the medical sensing field in general. The use of a sensor other than an ultrasound sensor is thus also contemplated, including the use of sensors of pressure, temperature, fluid flow, optical radiation, sound, or electrical signals. The sensing of physical parameters in applications such as blood flow sensing and thermometry is contemplated. Moreover, the use of interventional devices other than a medical needle is contemplated, including without limitation a catheter, a guidewire, a biopsy device, a pacemaker lead, an intravenous line or a surgical tool in general. The interventional device may be used in a wide variety or medical procedures, for example from routine needle insertion for regional anesthesia, to biopsies and percutaneous ablation of cancer, and in more advanced interventional procedures.

Figure 1:
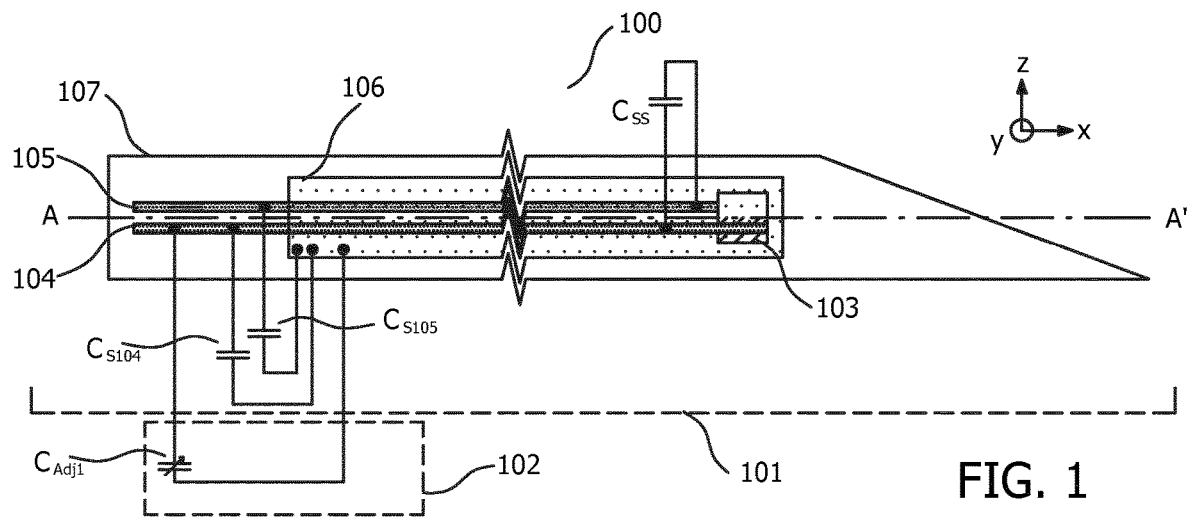
FIG. 1 illustrates a medical sensing system 100 that includes an elongate interventional device 101 and a first embodiment of an adjustable capacitance circuit 102.

Thereto, FIG. 1 illustrates a medical sensing system 100 that includes an elongate interventional device 101 and a first embodiment of an adjustable capacitance circuit 102. Elongate interventional device 101 in FIG. 1 includes sensor 103 that has a capacitance $C_{ss}$. Capacitance $C_{ss}$ is an inherent capacitance of the sensor itself. Sensor 103 is disposed on elongate interventional device 101. Elongate interventional device 101 in FIG. 1 also includes first electrical conductor 104 and second electrical conductor 105 that are in electrical contact with sensor 103 and extend along longitudinal axis A-A' of elongate interventional device 101 in order to providing electrical signals corresponding to signals detected by sensor 103. Elongate interventional device 101 also includes i) electrically conductive shield 106 that overlaps the electrical conductors 104, 105. The first electrical conductor 104 and the second electrical conductor 105 each have a stray capacitance $C_{S104}$, $C_{S105}$ to electrically conductive shield 106. Moreover, adjustable capacitance circuit 102 provides an adjustable capacitance $C_{Adj1}$ between electrical conductor 104 and i) electrically conductive shield 106 that overlaps electrical conductors 104, 105.

In the embodiment illustrated in FIG. 1, elongate interventional device 101 may be a medical needle and sensor 103 may be an ultrasound sensor having an inherent capacitance $C_{ss}$. Electrical conductors 104, 105 may for example be wires or other types of electrical conductors. By extending along longitudinal axis A-A' of elongate interventional device 101, electrical conductors 104, 105 provide electrical contact to sensor 103 at an axially-separated position along longitudinal axis A-A' to sensor 103. Electrically conductive shield 106 in FIG. 1 overlaps electrical conductors 104, 105 in order to reduce EMI to electrical signals present on electrical conductors 104, 105. In alternative implementations electrically conductive shield 106 may surround electrical conductors 104, 105 and/or interventional device 101. Moreover, whilst illustrated as overlapping sensor 103, electrically conductive shield 106 may alternatively not overlap sensor 103. Electrically conductive shield 106 may be formed from a layer or mesh of various types of electrical conductor, including metals such as copper, gold, silver, aluminium, conductive polymers and so forth. An insulator such as a polymer, not illustrated, may be disposed between electrical conductors 104, 105 and electrically conductive shield 106.

Electrically conductive shield 106 in FIG. 1 may significantly reduce EMI to electrical signals present on electrical conductors 104, 105. However, a secondary effect of its presence is the introduction of a stray capacitance, indicated as $C_{S104}$, $C_{S105}$ between each electrical conductor 104, 105, and electrically conductive shield 106. Differences between stray capacitances $C_{S104}$, $C_{S105}$ can result in different amounts of EMI being coupled to each electrical conductor 104, 105. This may result in sub-optimal EMI performance since common mode EMI on electrical conductors 104, 105 that is typically removed by differentially amplifying electrical signals on electrical conductors 104, 105 only removes the interference that is common to both electrical conductors. In FIG. 1, adjustable capacitance $C_{Adj1}$ between electrical conductor 104 and i) electrically conductive shield 106 that overlaps electrical conductors 104, 105 provides for the adjustment of differences between stray capacitances $C_{S104}$, $C_{S105}$, and consequently provides for a reduction in EMI to medical sensing system 100.

Various adjustable capacitances may be used to provide adjustable capacitance $C_{Adj1}$ illustrated in FIG. 1, including but not limited to a varactor diode—also known as a varicap diode/variable capacitance diode/variable reactance diode/ tuning diode, a mechanically-trimmed capacitor, a tunable micro-electro-mechanical systems i.e. MEMS capacitor, a Barium Strontium Titanate i.e. BST capacitor in which a capacitance is varied by applying high voltage, or a field effect transistor i.e. FET switch array.

Figure 2:
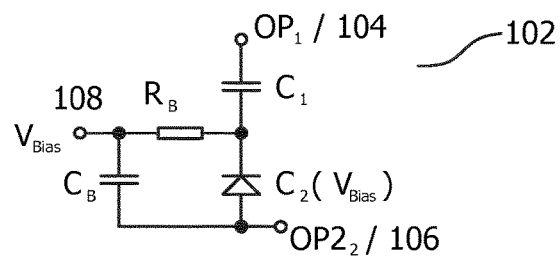
FIG. 2 illustrates and exemplary adjustable capacitance circuit 102 that may be used to provide adjustable capacitance $C_{Adj1}$ or $C_{Adj2}$ by means of a varactor diode.

In one exemplary implementation, FIG. 2 illustrates an exemplary adjustable capacitance circuit 102 that may be used to provide adjustable capacitance $C_{Adj1}$ or $C_{Adj2}$ by means of a varactor diode. Adjustable capacitance circuit 102 in FIG. 2 includes an input 108 for controlling, via bias voltage $V_{Bias}$, an adjustable capacitance $C_{Adj1}$ or $C_{Adj2}$ that is provided between output terminals $OP_1$, $OP_2$. Output terminals $OP_1$, $OP_2$ may respectively be connected to electrical conductor 104 and electrically conductive shield 106 in FIG. 1 in order to provide adjustable capacitance $C_{Adj1}$ therebetween. The diode in FIG. 2 operates as a varactor diode in which a capacitance across its terminals varies in accordance with the DC reverse bias voltage applied thereto; i.e. its capacitance $C_2$ is a function of $V_{Bias}$. Resistor RB and Capacitor CB act to provide, via voltage $V_{Bias}$, the bias voltage and thereby control over the capacitance across the terminals of the diode. Capacitor $C_1$ acts to isolate the bias voltage from terminal $OP_1$ and also contributes to the total capacitance $C_{Adj1}$ across terminals $OP_1$, $OP_2$. Consequently, $C_{Adj1}$ across terminals $OP_1$, $OP_2$ may be determined in accordance with the equation:

$$C_{Adj1} = \left[\frac{1}{c_1} + \frac{1}{c_2(v_{Bias})}\right]^{-1} \qquad \text{Equation 1}$$

Adjustable capacitance $C_{Adj1}$ may have any suitable value, and may include a fixed component and a variable component as indicated in Equation 1. In some implementations $C_{Adj1}$ may provide a value of a few picofarads or a few tens or hundreds of pico farads or a few nano farads or a few tens or hundreds of nano farads.

Adjustable capacitance circuit 102 in FIG. 2, or the aforementioned alternative adjustable capacitances, may also be used in adaptations of the medical sensing systems 100 illustrated in FIG. 1 in order to alternatively or additionally adjust the capacitance between electrical conductor 105 and electrically conductive shield 106 in FIG. 1, or the capacitance(s) between one or both of electrical conductors 104, 105 and ii) an electrically conductive shaft 107, in order to likewise reduce EMI.

Thus, in a variation of the implementation of FIG. 2, not illustrated, adjustable capacitance circuit 102 of FIG. 2 may alternatively be connected between electrical conductor 105 and electrically conductive shield 106 in order to adjust the capacitance therebetween. This may be useful when for instance a manufacturing process consistently results in a stray capacitance between electrical conductor 104 and electrically conductive shield 106 being lower than that between electrical conductor 105 and electrically conductive shield 106, and it is desired to provide a variable increase in the latter in order to reduce EMI.

Figure 3:
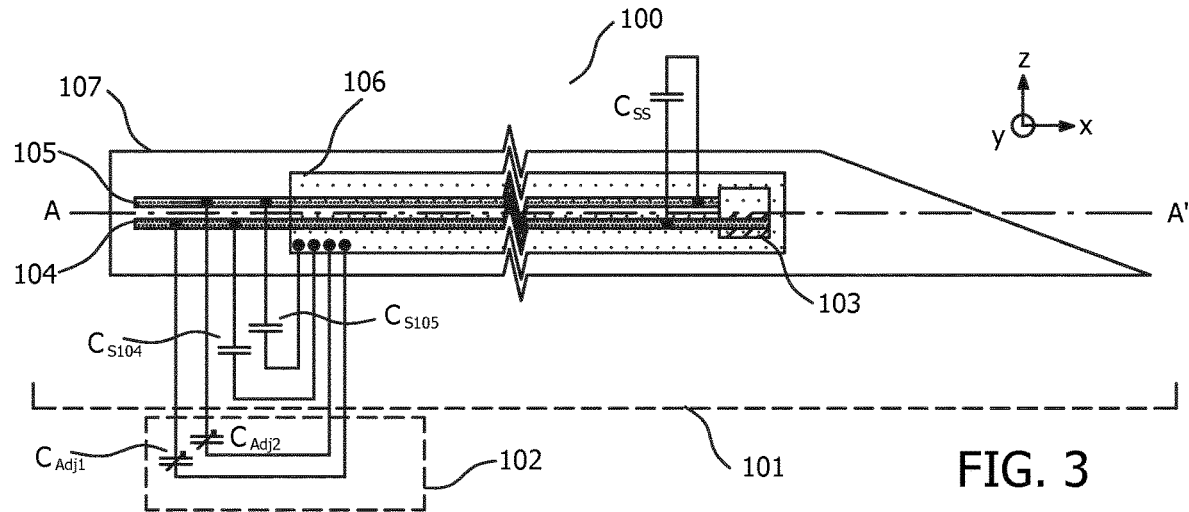
FIG. 3 illustrates a medical sensing system 100 that includes an elongate interventional device 101 and a second embodiment of an adjustable capacitance circuit 102.

In another example implementation, FIG. 3 illustrates a medical sensing system 100 that includes an elongate interventional device 101 and a second embodiment of an adjustable capacitance circuit 102. Figure references in FIG. 3 relate to the same items as described in relation to FIG. 1.

Adjustable capacitance circuit 102 in FIG. 3 includes two adjustable capacitances $C_{Adj1}$ and $C_{Adj2}$. Each adjustable capacitance $C_{Adj1}$ and $C_{Adj2}$ may exemplarily be provided by the circuit illustrated in FIG. 2 and used in a similar manner to that described in relation to FIG. 1 in order to further improve the control of EMI by providing control over the coupling of EMI from electrically conductive shield 106 to both electrical conductors 104, 105. In this implementation, adjustable capacitances $C_{Adj1}$ and $C_{Adj2}$ may be adjusted independently.

Figure 4:
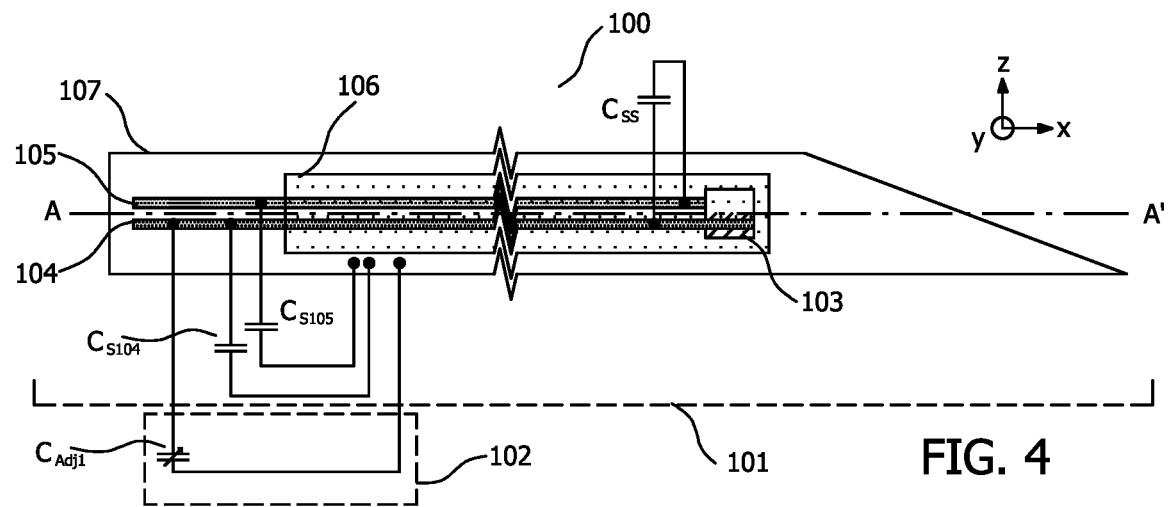
FIG. 4 illustrates a medical sensing system 100 that includes an elongate interventional device 101 and a third embodiment of an adjustable capacitance circuit 102.
Figure 5:
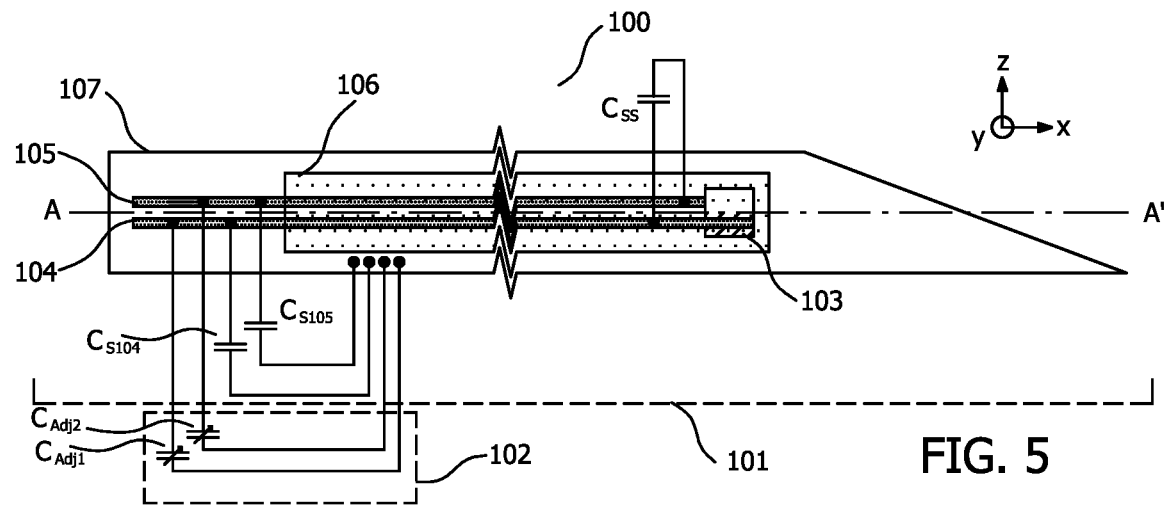
FIG. 5 illustrates a medical sensing system 100 that includes an elongate interventional device 101 and a fourth embodiment of an adjustable capacitance circuit 102.

It is also contemplated that the invention may be used with interventional devices having an electrically conductive shaft 107. Many interventional devices including medical needles, guidewires and so forth include such an electrically conductive shaft 107. EMI may alternatively or additionally couple to electrically conductive shaft 107, and subsequently couple to electrical conductors 104, 105 in differing amounts, thereby giving rise to different amounts of EMI on each electrical conductor as described above. With reference to FIG. 4 and FIG. 5, first electrical conductor 104 and second electrical conductor 105 may thus each have a stray capacitance $C_{S104}$, $C_{S105}$ to electrically conductive shaft 107. Whilst electrically conductive shield 106 is also illustrated in FIG. 4 and FIG. 5, this is entirely optional in these embodiments. FIG. 4 illustrates a medical sensing system 100 that includes an elongate interventional device 101 and a third embodiment of an adjustable capacitance circuit 102. In contrast to FIG. 1, the elongate interventional device 101 in FIG. 4 includes an electrically conductive shaft 107, and adjustable capacitance circuit 102 provides an adjustable capacitance $C_{Adj1}$ between electrical conductor 104 and electrically conductive shaft 107. In order to mitigate the coupling of different amounts of EMI to each of electrical conductors 104, 105, adjustable capacitance circuit 102 in FIG. 4 provides an adjustable capacitance $C_{Adj1}$ between electrical conductor 104 and ii) the electrically conductive shaft 107. Adjustable capacitance $C_{Adj1}$ may thus be used as described in relation to FIG. 1 and FIG. 2 to reduce EMI to electrical signals detected by sensor 103 in FIG. 4 by adjusting the total capacitance between electrical conductor 104 and electrically conductive shaft 107.

In a variation, not illustrated, of the implementation of FIG. 4, adjustable capacitance circuit 102 in FIG. 4 may alternatively be connected between electrical conductor 105 and electrically conductive shaft 107 in order to adjust the capacitance therebetween. This may be useful when for instance a manufacturing process consistently results in a stray capacitance between electrical conductor 104 and electrically conductive shaft 107 being lower than that between electrical conductor 105 and electrically conductive shaft 107, and it is desired to provide a variable increase in the latter in order to reduce EMI.

In another variation of the medical sensing system of FIG. 4, FIG. 5 illustrates a medical sensing system 100 that includes an elongate interventional device 101 and a fourth embodiment of an adjustable capacitance circuit 102. Figure references in FIG. 5 relate to the same items as described in relation to FIG. 4. In contrast to the medical sensing system of FIG. 4, in FIG. 5 adjustable capacitance circuit 102 includes two adjustable capacitances $C_{Adj1}$ and $C_{Adj2}$. Each adjustable capacitance $C_{Adj1}$ and $C_{Adj2}$ may exemplarily be provided by the circuit illustrated in FIG. 2 and used in a similar manner to that described in relation to FIG. 1 in order to further improve the control of EMI by providing control over the coupling of EMI from electrically conductive shaft 107 to both electrical conductors 104, 105.

Combinations of the aforementioned implementations of FIG. 1, and FIGS. 2-5 that implement the same principal of providing one or more adjustable capacitances $C_{Adj1}$, $C_{Adj2}$ between one or more of electrical conductors 104, 105 and i) electrically conductive shield 106 and/or electrically conductive shaft 107, are also contemplated, including the connection of an adjustable capacitance between one or more of electrical conductors 104, 105 and both electrically conductive shield 106 and electrically conductive shaft 107.

In order to provide optimal EMI reduction, $C_{Adj1}$ and/or $C_{Adj2}$ referred-to above may be adjusted in order to provide a similar, preferably the same, total capacitance between each electrical conductor 104, 105 and i) electrically conductive shield 106 that overlaps the electrical conductors 104, 105 and/or ii) electrically conductive shaft 107. This total capacitance comprises the combination of stray capacitance $C_{S104}$/$C_{S105}$, and its associated adjustable capacitance $C_{Adj1}$/$C_{Adj2}$. With reference to FIG. 2, this may be achieved by adjusting the bias voltage applied to $V_{Bias}$.

In some implementations it is contemplated to determine adjustable capacitance value $C_{Adj1}$, $C_{Adj2}$ during a calibration procedure, for example prior-to use, or when in-use, and during which the necessary capacitance value $C_{Adj1}$, $C_{Adj2}$ is e.g. adjusted or stored for later use. In other implementations the adjustment may be determined and made in-use, intermittently at predefined time intervals, or continuously, in order to accommodate temporal variations in stray capacitance or EMI coupling to electrical conductors 104, 105, for example due to bending of interventional device 101, and thereby improve the temporal EMI performance of the medical sensing system. Moreover, adjustable capacitance $C_{Adj1}$, $C_{Adj2}$ may alternatively be adjusted based on interference signals detected on each of electrical conductors 104, 105, or based on a measured difference between stray capacitances $C_{S104}$ and $C_{S105}$.

Figure 6:
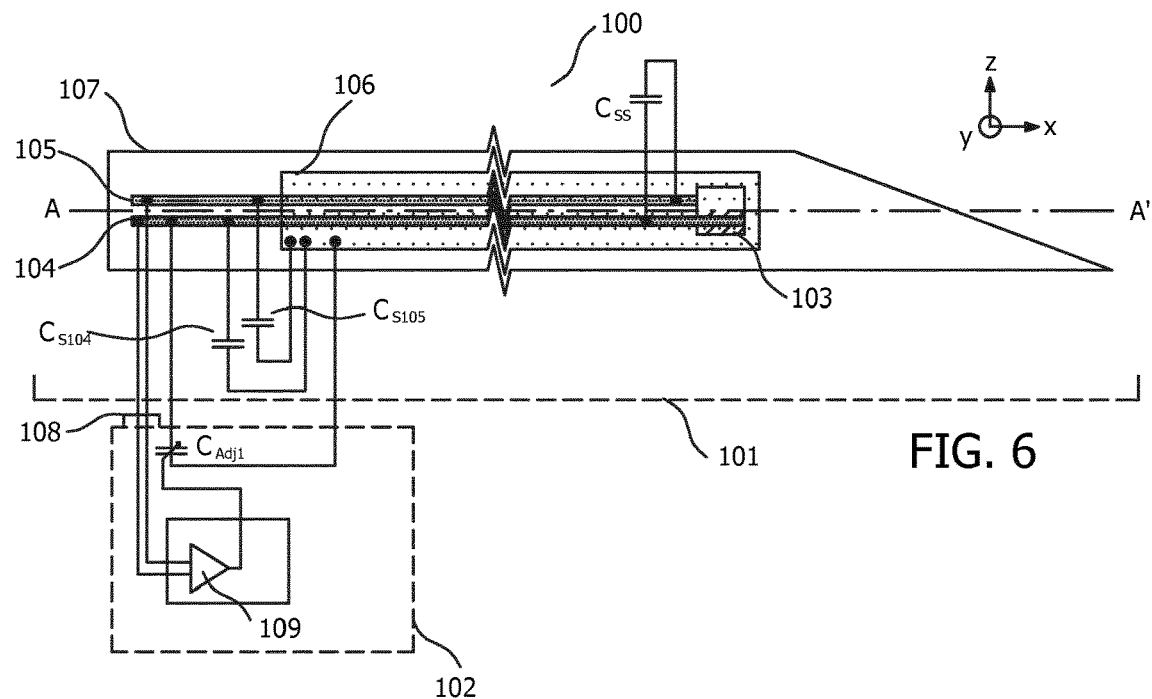
FIG. 6 illustrates a medical sensing system 100 that includes an elongate interventional device 101 and a fifth embodiment of an adjustable capacitance circuit 102 that includes two inputs 108.

In this regard, FIG. 6 illustrates a medical sensing system 100 that includes an elongate interventional device 101 and a fifth embodiment of an adjustable capacitance circuit 102 that includes two inputs 108. The two inputs 108 in FIG. 6 receive electrical signals indicative of interference signals detected respectively on first electrical conductor 104 and on second electrical conductor 105. Moreover, adjustable capacitance circuit 102 controls adjustable capacitance $C_{Adj1}$ based on the detected interference signals. In this implementation unit 109 may for example include a differential amplifier, the term amplifier defined herein to include a unity gain buffer, as well as amplifiers with gain values different to unity, which differential amplifier provides an output that controls adjustable capacitance $C_{Adj1}$.

In this implementation the use of a differential amplifier that connects to electrical conductors 104, 105 inherently provides a signal corresponding to the difference in interference on these conductors. The output of the differential amplifier may then be suitably processed, for example by (bandpass) filtering the signal in order to distinguish interference from any desired sensor signal that may be present on these electrical conductors, and e.g. determining its average or root mean square value, such that it may be used to generate bias voltage $V_{Bias}$ to adjustable capacitance circuit 102 in FIG. 2.

In one implementation of the adjustable capacitance circuit 102 that does not use a differential amplifier, an analogue-to-digital converter may alternatively be used to directly convert the measured interference values on one or both of electrical conductors 104, 105 in order to generate bias voltage $V_{Bias}$ for adjustable capacitance circuit 102 in FIG. 2. An interference value measured on only one of the conductors 104, 105, or indeed the difference between interference values measured on both conductors 104, 105 may be used in this manner. In another implementation of the adjustable capacitance circuit 102 that does not use a differential amplifier the electrical signals on each electrical conductor 104, 105 may be measured separately, optionally after suitable buffering or amplification, and then subtracted in order to generate bias voltage $V_{Bias}$ to adjustable capacitance circuit 102 in FIG. 2. Alternatively the interference on only one of the electrical conductors 104, 105 may be measured and this may then be used in a similar manner to generate bias voltage $V_{Bias}$ to adjustable capacitance circuit 102 in FIG. 2. This latter implementation may be particularly useful when for example it is known that one of the stray capacitance values $C_{S104}$, $C_{S10}$, is consistently the lower of the two.

In so doing a reliable technique of reducing EMI is provided because it is based on the actual detected interference. As mentioned above, in some implementations it is contemplated to determine adjustable capacitance value $C_{Adj1}$, $C_{Adj2}$ during a calibration procedure, for example prior-to use, or when in-use, and during which the necessary capacitance value $C_{Adj1}$, $C_{Adj2}$ is e.g. adjusted or stored for later use. In other implementations the adjustment may be determined and made in-use, intermittently at predefined time intervals, or continuously.

In another implementation, not illustrated, adjustable capacitance circuit 102 is configured to control adjustable capacitance $C_{Adj1}$, $C_{Adj2}$ based on a difference in stray capacitance, i.e. $C_{S104}$, $C_{S105}$, measured between each electrical conductor 104, 105 and i) electrically conductive shield 106 that overlaps electrical conductors 104, 105 and/or ii) electrically conductive shaft 107. Well-known capacitance measuring techniques may be used to determine the stray capacitances $C_{S104}$, $C_{S105}$. As with the measured interference, in some implementations it is contemplated to determine adjustable capacitance value $C_{Adj1}$, $C_{Adj2}$ during a calibration procedure, for example prior-to use, or when in-use, and during which the necessary capacitance value $C_{Adj1}$, $C_{Adj2}$ is e.g. adjusted or stored for later use. In other implementations the adjustment may be determined and made in-use, intermittently at predefined time intervals, or continuously.

Figure 7:
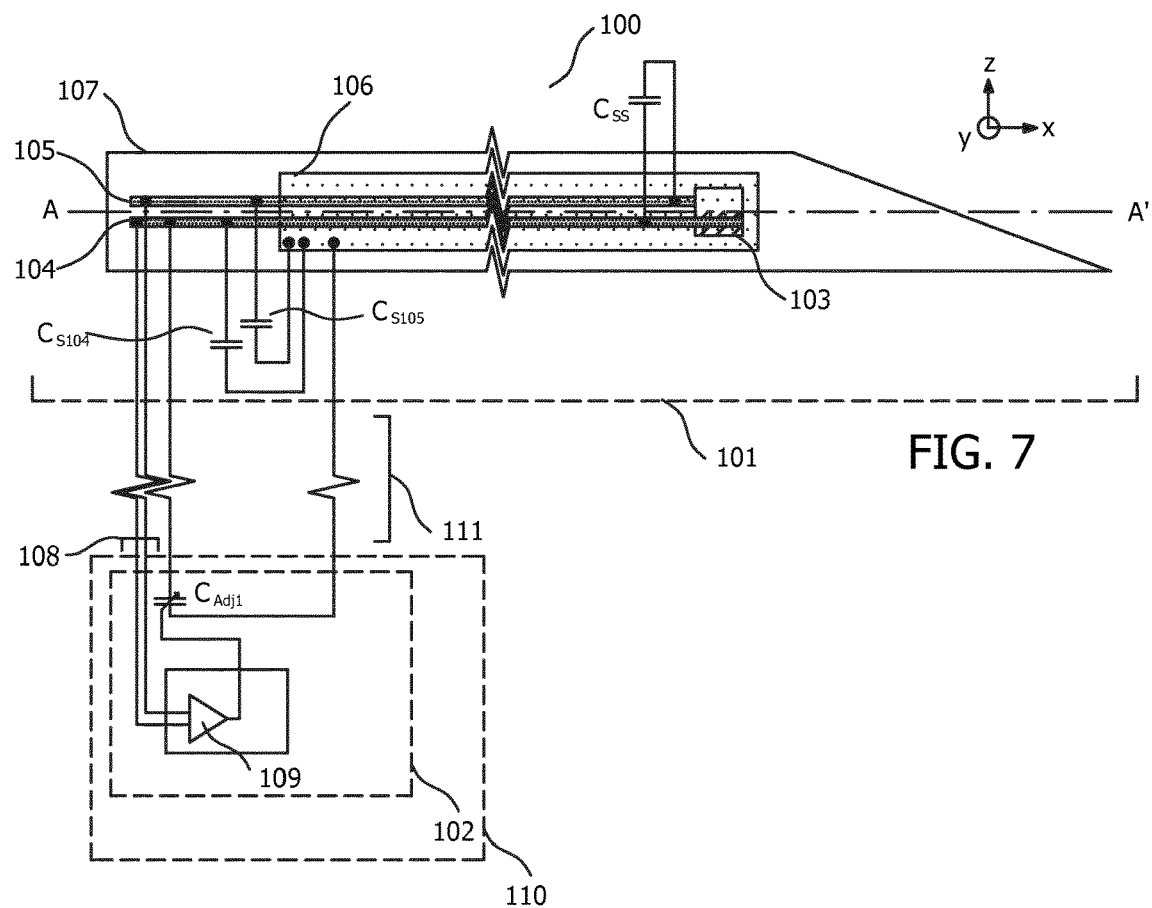
FIG. 7 illustrates a medical sensing system 100 that includes an elongate interventional device 101 and a sixth embodiment of an adjustable capacitance circuit 102 that includes a differential amplifier 109.

In one implementation, medical sensing system 100 includes a differential amplifier. Thereto, FIG. 7 illustrates a medical sensing system 100 that includes an elongate interventional device 101 and a sixth embodiment of an adjustable capacitance circuit 102 that includes a differential amplifier 109. Differential amplifier 109 is in electrical communication with each of first electrical conductor 104 and second electrical conductor 105 and provides an output signal corresponding to an amplified difference between an electrical signal on the first electrical conductor 104 and an electrical signal on the second electrical conductor 105. In some implementations the differential amplifier may be a differential charge amplifier, particularly in view of the capacitance of sensor $C_{ss}$, although in other implementations a differential current or voltage amplifier may be used. The output signal of the differential amplifier may, as described above, be used to control adjustable capacitance(s) $C_{Adj1}$ and/or $C_{Adj2}$. Moreover, the differential amplifier may also be used to provide a sensor signal. Using the differential amplifier to provide both the sensor signal and to control the adjustable capacitance $C_{Adj1}$, $C_{Adj2}$ advantageously reduces the complexity of the electronic circuitry associated with medical sensing system 100.

It is to be noted that the embodiments of FIG. 6 and FIG. 7 may alternatively be used in implementations having an electrically conductive shaft 107, wherein stray capacitances $C_{S104}$, $C_{S105}$ and adjustable capacitance(s) $C_{Adj1}$ and/or $C_{Adj2}$ are alternatively electrically connected to electrically conductive shaft 107.

In some implementations, elongate interventional device 101 includes both i) an electrically conductive shield 106 that overlaps the electrical conductors 104, 105 and ii) an electrically conductive shaft 107. Moreover, electrically conductive shield 106 may be electrically connected to electrically conductive shaft 107. Preferably this electrical connection is made via a conductive trace such as a wire and so forth. Connecting these two items together has been found to further reduce EMI to the electrical signals detected by electrical conductors 104, 105. Moreover, such a connection may reduce the complexity of the electrical shielding and provides for a more flexible interconnection between the medical sensing system and adjustable capacitance circuit 102 since only a single electrical conductor is required to shield the electrical signals between these two items.

In this regard, FIG. 7 also illustrates optional electrical cable 111 and optional console/electrical connector 110. Adjustable capacitance circuit 102 may be disposed in the console or the electrical connector 110. In this implementation, electrical cable 111 connects adjustable capacitance circuit 102 to first electrical conductor 104 and to second electrical conductor 104 and to i) electrically conductive shield 106 that overlaps electrical conductors 104, 105 and/or ii) electrically conductive shaft 107. Disposing adjustable capacitance circuit 102 in the console or in the connector, rather than for example on interventional device 101 may allow adjustable capacitance circuit 101 to be re-used. For example the connector may be a two-part connector wherein a first part is connected to interventional device 102 by means of electrical cable 111 and a second part, within which adjustable capacitance circuit 102 is disposed, may be temporarily attached to the first part. The second part may include a separate connector cable for making electrical connection to a console. This allows for the disposal of interventional device 102, together with electrical cable 111 and the first part of the connector, and the re-use of the second part of the connector.

One exemplary technique for disposing aforementioned sensor 103 on interventional device 101 is now illustrated with reference to FIG. 8 and FIG. 9. Alternative techniques also exist, including the mounting of a discrete sensor 103 on elongate interventional device 101 by means of an adhesive and attaching electrical conductors 104, 105 lengthwise along elongate interventional device 101, and so FIG. 8 and FIG. 9 are purely intended to be illustrative of a preferred implementation. Thereto, FIG. 8 illustrates various views of a sensor strip 800 that includes sensor 103; and FIG. 9 illustrates an exemplary interventional device 101 that has sensor strip 800 wrapped around its shaft in the form of a spiral. Interventional device 101 in FIG. 9 includes longitudinal axis A-A', and sensor strip 800 includes sensor 103, first electrical conductor 104, second electrical conductor 105, first polymer layer 125, second polymer layer 126 and optional electrically conductive shield 106. First electrical conductor 104, second electrical conductor 105 and sensor 103 are disposed between first polymer layer 125 and second polymer layer 126 and on a first side of first polymer layer 125. Optional electrically conductive shield 106 may be disposed on a second, i.e. opposing side of first polymer layer 125. In FIG. 8A a plan view of sensor strip 800 is illustrated, and sections through sensor strip 800 at B-B', C-C' and D-D' are illustrated in FIG. 8B, FIG. 8C and FIG. 8D respectively. Exploded sections through sensor strip 800 at B-B' and C-C' are illustrated in FIG. 8B' and FIG. 8C' respectively. With reference to FIG. 8A and FIG. 8C in particular, first electrical conductor 104, second electrical conductor 105 and sensor 103 are disposed between first polymer layer 125 and second polymer layer 126 and on a first side of first polymer layer 125 in sensor region C-C', that includes sensor 102. Optional electrically conductive shield layer 106 is disposed on the second, i.e. the opposing side of first polymer layer 125 in sensor region C-C'. As seen in particular in FIG. 8C, first electrical conductor 104 and second electrical conductor 105 are in electrical contact with sensor 103 and, as seen in particular in FIG. 8A and FIG. 8D, they extend along a length direction 124 of sensor strip 800 between sensor region C-C' and contact region D-D' within which first polymer layer 125 and electrically conductive shield 126 are removed for exposing a portion of electrical conductors 104, 105. With reference to FIG. 9, sensor strip 800 is wrapped around longitudinal axis A-A' of elongate interventional device 101 in the form of a spiral such that optional electrically conductive shield 106 faces outwards, and such that first electrical conductor 104 and second electrical conductor 105 both extend along longitudinal axis A-A'.

Polymer layers 125, 126 in sensor strip 800 may be formed from a range of polymers including but not limited to polyethylene terephthalate, PET, polyimide, PI, or polyamide, PA. Moreover, polymer layers 125, 126 may include an adhesive coating, optionally a pressure sensitive adhesive coating, on one or both of their surfaces, these being illustrated as adhesive layers 127, 128, 128, 130 in FIG. 8. The adhesives act to bond each of the polymer layers together. Adhesive layer 130 may be used to attach sensor strip 800 to elongate interventional device 101. Pressure sensitive adhesives are a class of materials that form an adhesive bond upon application of pressure. The 3M Corporation, USA is one suitable supplier of PSA-coated polymer sheets. Polymer layers with PSA on one or both surfaces may be used. PSA-coated polymer sheets are typically provided with a removable release layer that is peeled away to reveal the adhesive coating and thereby protect the adhesive layer until its adhesive properties are required. Optional conductive electrodes 131, 132 are also illustrated in FIG. 8 and serve to improve electrical contact to sensor 103.

In one specific implementation, sensor 103 is formed from a piezoelectric material. Various so-called hard or soft piezoelectric materials may be used. The piezoelectric material may for example be a polymer such as Polyvinylidene fluoride, i.e. PVDF, PVDF co-polymer such as polyvinylidene fluoride trifluoroethylene (P(VDF-TrFE)) layer, or PVDF ter-polymer such as P(VDF-TrFE-CTFE). Such PVDF materials are available as a layer that may be incorporated within polymer layers 125, 126. Such PVDF materials may for example detect ultrasound signals, sound, or pressure. Sensor 103 may for example be another type of ultrasound sensor such as a capacitive micromachined ultrasound transducer, i.e. a CMUT, or another type of sensor altogether.

With reference to FIG. 9, by suitably setting acute angle α and the width dimension W of sensor strip 104, sensor 103 may be provided in the form of a band around elongate interventional device 101. Sensor strip 800 includes first edge 121 and opposing second edge 122, these edges being separated by width dimension W. First edge 121 and second edge 122 each extend along length direction 124 of transducer strip 800. Length direction 124 is orthogonal to the direction in which width dimension W is measured. Sensor strip 800 may be wrapped around longitudinal axis A-A' such that sensor strip direction 123 lies in a plane that is normal to longitudinal axis A-A'. The wrapping may be such that adjacent wrapped turns either abut one another, just overlap, or have a gap between one another. In order for consecutive turns of the spiral to abut, i.e. just touch, one another, the following equation should be satisfied:

$$W = \pi \cdot D \cdot \sin(\alpha) \qquad \text{Equation 1}$$

wherein α is the acute angle defined above with respect to length direction 124, and D is the diameter of a circular cross section of elongate interventional device 101. By arranging that W exceeds the above value, consecutive turns of the spiral overlap one another. Likewise by arranging that W is less than this value a small gap may be provided between consecutive turns of the spiral.

Figure 10:
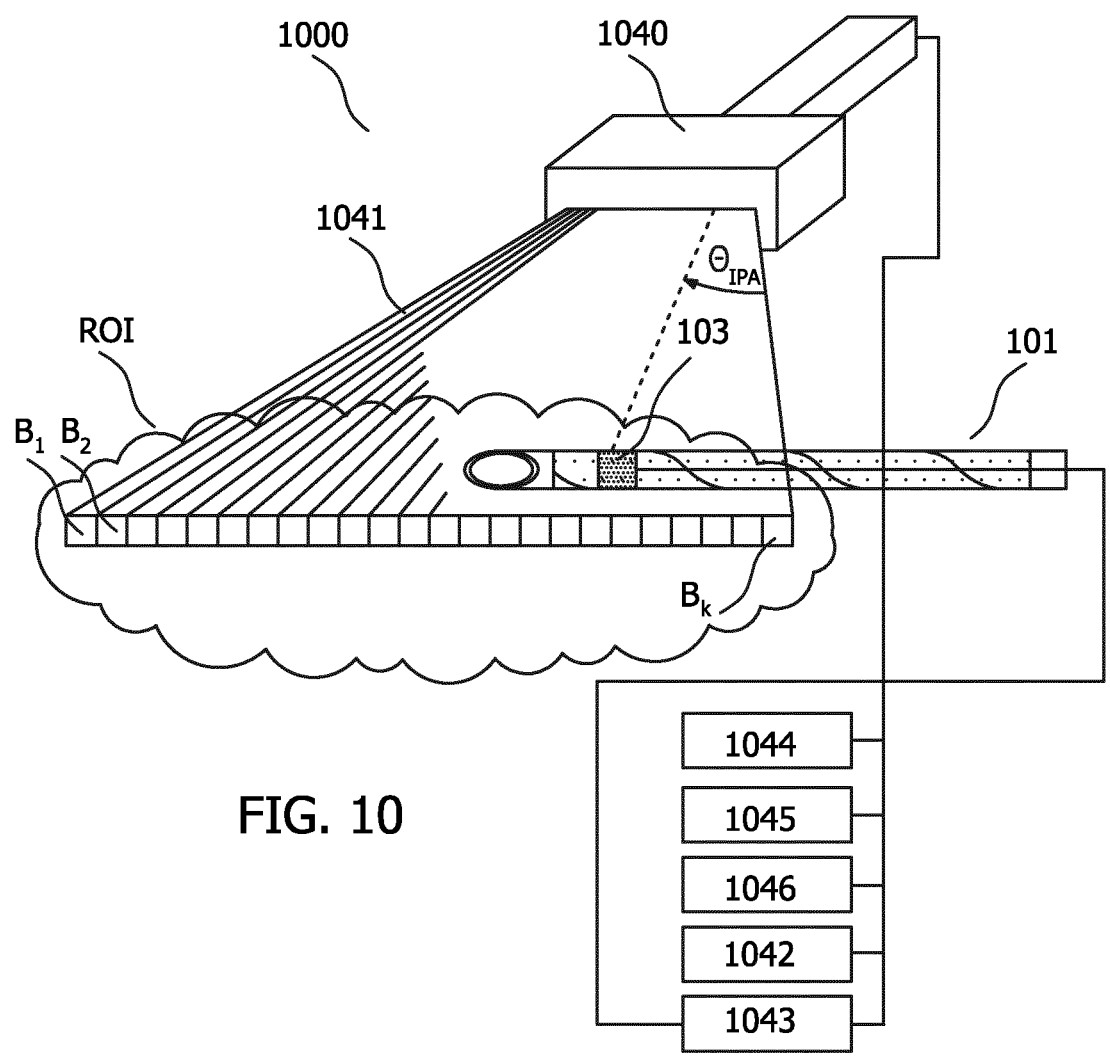
FIG. 10 illustrates an ultrasound-based position determination system 1000 that includes elongate interventional device 101.

Medical sensing system 100 described above finds application in many areas in the medical field. One particular application is now described with reference to FIG. 10, which illustrates an ultrasound-based position determination system 1000 that includes elongate interventional device 101. Ultrasound-based position determination system 1000 also includes beamforming ultrasound imaging probe 1040, image reconstruction unit 1042, and position determination unit 1043. Sensor 103 in FIG. 10 is an ultrasound sensor. A PVDF piezoelectric sensor, or a CMUT, device are non-limiting examples of suitable ultrasound sensors. Beamforming ultrasound imaging probe 1040 is configured to generate an ultrasound field 1041. Image reconstruction unit 1042 is configured to provide a reconstructed ultrasound image corresponding to the ultrasound field 1041 of beamforming ultrasound imaging probe 1040. Position determination unit 1043 is configured to compute a position of ultrasound sensor 103 respective ultrasound field 1041 based on ultrasound signals transmitted between beamforming ultrasound imaging probe 1040 and ultrasound sensor 103, and to provide an icon in the reconstructed ultrasound image based on the computed position of ultrasound sensor 103. Optional display 1044, imaging system interface 1045, and imaging system processor 1046 illustrated in FIG. 10 may also be included Links between the various units illustrate their respective communication links.

Together, units 1040, 1042, 1044, 1045 and 1046 form a conventional ultrasound imaging system. The units 1042, 1044, 1045 and 1046 are conventionally located in a console that is in wired or wireless communication with beamforming ultrasound imaging probe 1040. Some of units 1042, 1044, 1045 and 1046 may alternatively be incorporated within beamforming ultrasound imaging probe 1040 as for example in the Philips Lumify ultrasound imaging system. Beamforming ultrasound imaging probe 1040 generates ultrasound field 1041. In FIG. 10, a 2D beamforming ultrasound imaging probe 1040 is illustrated that includes a linear ultrasound transceiver array that transmits and receives ultrasound energy within an ultrasound field 1041 which intercepts region of interest ROI. The ultrasound field is fan-shaped in FIG. 10 and includes multiple ultrasound beams $B_{1..k}$ that together provide the illustrated image plane. Note that whilst FIG. 10 illustrates a fan-shaped beam the invention is not limited to use with a particular shape of ultrasound field or indeed to a planar ultrasound field. Beamforming ultrasound imaging probe 1040 may also include electronic driver and receiver circuitry, not shown, that is configured to amplify and/or to adjust the phase of signals it transmits or receives in order to generate and detect ultrasound signals in ultrasound beams $B_{1..k}$.

In-use the above-described conventional ultrasound imaging system is operated in the following way. An operator may plan an ultrasound procedure via imaging system interface 1045. Once an operating procedure is selected, imaging system interface 1045 triggers imaging system processor 1046 to execute application-specific programs that generate and interpret the signals transmitted to and detected by beamforming ultrasound imaging probe 1040. A memory, not shown, may be used to store such programs. The memory may for example store ultrasound beam control software that is configured to control the sequence of ultrasound signals transmitted by and/or received by beamforming ultrasound imaging probe 1040. Image reconstruction unit 1042 provides a reconstructed ultrasound image corresponding to ultrasound field 1041 of beamforming ultrasound imaging probe 1040. Image reconstruction unit 1042 thus provides an image corresponding to the image plane defined by ultrasound field 1041 and which intercepts region of interest ROI. The function of image reconstruction unit 1042 may alternatively be carried out by imaging system processor 1046. The image may subsequently be displayed on display 1044. The reconstructed image may for example be an ultrasound Brightness-mode "B-mode" image, otherwise known as a "2D mode" image, a "C-mode" image or a Doppler mode image, or indeed any ultrasound image.

Also shown in FIG. 10 is elongate interventional device 101, exemplified by a medical needle, which includes ultrasound sensor 103. Adjustable capacitance circuit 102, not illustrated, which together with interventional device 101 forms medical sensing system 100, may be disposed between elongate interventional device 101 and position determination unit 1043, for example in a connector that may be disposed in a connectors between these two units as described above, or in a console that houses units 1042, 1044, 1045 and 1046 as described above. In this exemplary application, elongate interventional device 101, or more specifically ultrasound sensor 103 disposed thereon, may be tracked respective ultrasound field 1041 based on signals provided by position determination unit 1043. Position determination unit 1043 is in communication with ultrasound sensor 103, which communication may for example be wired or wireless. The function of position determination unit 1043 may in some implementations be carried out by a processor of the conventional ultrasound imaging system.

In-use, a position of ultrasound sensor 103 is computed respective ultrasound field 1041 by position determination unit 1043 based on ultrasound signals transmitted between beamforming ultrasound imaging probe 1040 and ultrasound sensor 103. Ultrasound sensor 103 detects ultrasound signals corresponding to beams $B_{1..k}$. Position determination unit 1043 identifies the position of ultrasound sensor 103 based on i) the amplitudes of the ultrasound signals corresponding to each beam $B_{1..k}$ that are detected by ultrasound sensor 103, and based on ii) the time delay, i.e. time of flight, between emission of each beam $B_{1..k}$ and its detection by ultrasound sensor 103. Position determination unit 1043 subsequently provides an icon in the reconstructed ultrasound image based on the computed position of ultrasound sensor 103. The icon may for example indicate the computed position of ultrasound sensor 103. The icon may also optionally indicate a range of positions within which a portion of the interventional device, e.g. its distal end, may lie. More specifically the position is computed by finding the best fit position of ultrasound sensor 103 respective ultrasound field 1041 based on the detected ultrasound signals.

This may be illustrated as follows. When ultrasound sensor 103 is in the vicinity of ultrasound field 1041, ultrasound signals from the nearest of beams $B_{1..k}$ to the sensor will be detected with a relatively larger amplitude whereas more distant beams will be detected with relatively smaller amplitudes. Typically the beam that is detected with the largest amplitude is identified as the one that is closest to ultrasound sensor 103. This beam defines in-plane angle $\theta_{IPA}$ between beamforming ultrasound imaging probe 1040 and ultrasound sensor 103. The corresponding range depends upon the time delay, i.e. the time of flight, between the emission of the largest-amplitude beam $B_{1..k}$ and its subsequent detection. The range may thus be determined by multiplying the time delay by the speed of ultrasound propagation. Thus, the range and corresponding in-plane angle $\theta_{IPA}$ of the beam detected with the largest amplitude can be used to identify the best-fit position of ultrasound sensor 103 respective ultrasound field 1041.

Whilst reference has been made above to a planar ultrasound imaging probe in the above it is to be appreciated that the exemplified beamforming ultrasound imaging probe 1040 is only one example of a beamforming ultrasound imaging probe in which elongate interventional device 101 may be used. Elongate interventional device 101 also finds application in ultrasound-based position determination systems that include other types of 2D or 3D beamforming ultrasound imaging probes. These may include for example a "TRUS" transrectal ultrasonography probe, an "IVUS" intravascular ultrasound probe, a "TEE" transesophageal probe, a "TTE" transthoracic probe, a "TNE" transnasal probe, an "ICE" intracardiac probe. Moreover, it is to be appreciated that elongate interventional device 101 also finds application in other ultrasound sensing applications in the medical field beyond position tracking.

In accordance with some implementations an interference reduction method is provided for use in medical sensing system 100 that includes sensor 103 having capacitance $C_{ss}$ disposed on elongate interventional device 101, and first electrical conductor 104 and second electrical conductor 105, first electrical conductor 104 and second electrical conductor 105 being in electrical contact with sensor 103 and extending along elongate interventional device 101 for providing electrical signals corresponding to signals detected by sensor 103, and i) an electrically conductive shield 106 that overlaps electrical conductors 104, 105 and/or ii) an electrically conductive shaft 107 and in which first electrical conductor 104 and second electrical conductor 105 each have a stray capacitance $C_{S104}$, $C_{S105}$ to electrically conductive shield 106 and/or to electrically conductive shaft 107. The method comprises the steps of:

adjusting a capacitance $C_{Adj1}$, $C_{Adj2}$ between at least one of the electrical conductors 104, 105 and i) the electrically conductive shield 106 that overlaps electrical conductors 104, 105 and/or ii) electrically conductive shaft 107, such that a magnitude of interference to the electrical signals on at least one of the electrical conductors 104, 105 is adjusted.

Preferably the interference to the electrical signals on both of the electrical conductors 104, 105, is reduced.

The method may further include the steps of:
receiving signals indicative of detected interference on at least one of the electrical conductors 104, 105; and adjusting the capacitance $C_{Adj1}$, $C_{Adj2}$ based on the received signals.

Again, preferably the capacitance $C_{Adj1}$, $C_{Adj2}$ is adjusted such that the interference to the electrical signals on both of the electrical conductors 104, 105, is reduced.

This interference reduction method may for example be implemented by a processor that controls an analogue to digital converter for digitizing the electrical signals on electrical conductors 104, 105 and thus determining the detected interference, and which also controls the aforementioned adjustable capacitance circuit 102.

Moreover, any of the method steps disclosed herein, particularly those described in relation to the processor of position determination unit 1043 in FIG. 10, and the interference reduction method may be recorded in the form of instructions which when executed on a processor cause the processor to carry out such method steps in combination with the described hardware. The instructions may be stored on a computer program product. The computer program product may be provided by dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor "DSP" hardware, read only memory "ROM" for storing software, random access memory "RAM", non-volatile storage, etc. Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system, or apparatus or device, or a propagation medium. Examples of a computer-readable medium include a semiconductor or solid state memory, magnetic tape, a removable computer diskette, a random access memory "RAM", a read-only memory "ROM", a rigid magnetic disk and an optical disk. Current examples of optical disks include compact disk-read only memory "CD-ROM", compact disk-read/write "CD-R/W", Blu-Ray™ and DVD.

In summary, a medical sensing system has been provided that includes an elongate interventional device and an adjustable capacitance circuit. The elongate interventional device includes a sensor having a capacitance. The sensor is disposed on the elongate interventional device. The elongate interventional device also includes a first electrical conductor and a second electrical conductor, the first electrical conductor and the second electrical conductor being in electrical contact with the sensor and extending along the elongate interventional device for providing electrical signals corresponding to signals detected by the sensor. The elongate interventional device also includes i) an electrically conductive shield that overlaps the electrical conductors and/or ii) an electrically conductive shaft. The first electrical conductor and the second electrical conductor each have a stray capacitance to the electrically conductive shield and/or to the electrically conductive shaft. The adjustable capacitance circuit provides an adjustable capacitance between at least one of the electrical conductors and i) the electrically conductive shield that overlaps the electrical conductors and/or ii) the electrically conductive shaft.

Various embodiments and options have been described in relation to the medical sensing system, and it is noted that the various embodiments may be combined to achieve further advantageous effects. In particular it is noted that any of the features described in relation to the medical sensing system disclosed may be implemented in the aforementioned method. Any reference signs in the claims should not be construed as limiting the scope of the invention.

As used herein, the term "or" should be interpreted as a disjunctive "or." Further, the term "or" and the term "and" when prefaced by the term "at least one of" or the term by "one or more of" should be interpreted as a disjunctive list such that, for example, a list of "at least one of A or B" or a list of "one or more of A and B" or a list of "A or B" should be interpreted to include either A or B, one of A and one of B, a combination of one or more of each of A and B; both A and B; or combinations of one or more of A and B, and such other combinations as relevant to the recited list or terms consistent with the corresponding description in the specification.

The invention claimed is:

1. A medical sensing system comprising:
an elongate interventional device comprising:
a sensor having a capacitance, the sensor disposed on the elongate interventional device;
a first electrical conductor and a second electrical conductor in electrical contact with the sensor, extending along the elongate interventional device, and configured to provide electrical signals corresponding to signals detected by the sensor; and
at least one of an electrically conductive shield overlapping both the first electrical conductor and the second electrical conductor or an electrically conductive shaft, wherein the first electrical conductor and the second electrical conductor each have a stray capacitance to at least one of the electrically conductive shield or to the electrically conductive shaft; and
an adjustable capacitance circuit configured to:
measure a difference in the stray capacitance between each of the first electrical conductor and the second electrical conductor and at least one of the electrically conductive shield or the electrically conductive shaft, and
control an adjustable capacitance, between at least one of the first electrical conductor or the second electrical conductor and at least one of the electrically conductive shield or the electrically conductive shaft, based on the measured difference in stray capacitance.

2. The medical sensing system according to claim 1, wherein the adjustable capacitance circuit is further configured to control the adjustable capacitance such that a substantially equal total capacitance is provided between each of the first electrical conductor and the second electrical conductor and at least one of the electrically conductive shield or electrically conductive shaft.

3. The medical sensing system according to claim 1, wherein the adjustable capacitance circuit is further configured to:
receive electrical signals indicative of interference signals detected on the first electrical conductor or on the second electrical conductor; and
control the adjustable capacitance based on the detected interference signals.

4. The medical sensing system according to claim 1, wherein the adjustable capacitance circuit comprises a varactor diode.

5. The medical sensing system according to claim 1, further comprising:
a differential amplifier in electrical communication with each of the first electrical conductor and the second electrical conductor, the differential amplifier configured to provide an output signal corresponding to an amplified difference between an electrical signal on the first electrical conductor and an electrical signal on the second electrical conductor.

6. The medical sensing system according to claim 1, wherein the elongate interventional device comprises both the electrically conductive shield and the electrically conductive shaft, and
the electrically conductive shield is electrically connected to the electrically conductive shaft.

7. The medical sensing system according to claim 1, wherein the sensor is configured to detect ultrasound signals.

8. The medical sensing system according to claim 1, further comprising:
a console or an electrical connector, wherein the adjustable capacitance circuit is disposed in the console or the electrical connector; and
an electrical cable configured to connect the adjustable capacitance circuit to the first electrical conductor, to the second electrical conductor, and to at least one of the electrically conductive shield or the electrically conductive shaft.

9. The medical sensing system according to claim 1, wherein the sensor is an ultrasound sensor, and the system further comprising:
a beamforming ultrasound imaging probe configured to generate an ultrasound field;
an image reconstruction processor configured to provide a reconstructed ultrasound image corresponding to the ultrasound field of the beamforming ultrasound imaging probe; and
a position determination processor configured to:
compute a position of the ultrasound sensor of the interventional device relative to the ultrasound field based on ultrasound signals transmitted between the beamforming ultrasound imaging probe and the ultrasound sensor, and to
provide an icon in the reconstructed ultrasound image based on the computed position of the ultrasound sensor.

10. A method for reducing interference of electrical signals, the method comprising:
providing an interventional device that includes:
a sensor disposed on an elongate interventional device and having a capacitance,
a first electrical conductor and a second electrical conductor in electrical contact with the sensor, the first electrical conductor and the second electrical conductor extending along the elongate interventional device and configured to provide electrical signals corresponding to signals detected by the sensor, and
at least one of an electrically conductive shield overlapping both the first electrical conductor and a second electrical conductor or an electrically conductive shaft, wherein
the first electrical conductor and the second electrical conductor each have a stray capacitance to at least one of the electrically conductive shield or to the electrically conductive shaft;
measuring a difference in stray capacitance between each of the first electrical conductor and the second electrical conductor and at least one of the electrically conductive shield or the electrically conductive shaft; and
adjusting a capacitance, between at least one of the first electrical conductor or the second electrical conductor and at least one of the electrically conductive shield or the electrically conductive shaft, based on the measured difference in stray capacitance.

11. The method according to claim 10, further comprising:
receiving signals indicative of detected interference on at least one of the first electrical conductor or the second electrical conductor; and
adjusting the capacitance based on the received signals.

12. A non-transitory computer readable medium having stored thereon instructions which when executed on a processor, cause the processor to:
detect an interventional device that includes:
a sensor disposed on an elongate interventional device and having a capacitance, and
a first electrical conductor and a second electrical conductor in electrical contact with the sensor, the first electrical conductor and the second electrical conductor extending along the elongate interventional device and configured to provide electrical signals corresponding to signals detected by the sensor, and
at least one of an electrically conductive shield overlapping both the first electrical conductor and a second electrical conductor or an electrically conductive shaft, wherein the first electrical conductor and the second electrical conductor each have a stray capacitance to at least one of the electrically conductive shield or to the electrically conductive shaft;
measure a difference in stray capacitance between each of the first electrical conductor and the second electrical conductor and at least one of the electrically conductive shield or the electrically conductive shaft; and
adjust a capacitance, between at least one of the first electrical conductor or the second electrical conductor and at least one of the electrically conductive shield or the electrically conductive shaft, based on the measured stray capacitance.

13. The non-transitory computer readable medium according to claim 12, further comprising instructions that, when executed by the processor, further cause the processor to:
receive signals indicative of detected interference on at least one of the first electrical conductor or the second electrical conductor; and
adjust the capacitance based on the received signals.

14. The non-transitory computer readable medium according to claim 12, further comprising instructions that, when executed by the processor, further cause the processor to output a signal corresponding to an amplified difference between an electrical signal on the first electrical conductor and an electrical signal on the second electrical conductor.

15. The non-transitory computer readable medium according to claim 12, wherein the sensor is an ultrasound sensor and the non-transitory computer readable medium further comprising instructions that, when executed by the processor, further cause the processor to:

communicate with an ultrasound imaging probe configured to generate an ultrasound field, the computer readable medium further comprising instructions that, when executed by the processor, further cause the processor to:
reconstruct an ultrasound image corresponding to the ultrasound field of the beamforming ultrasound imaging probe; and
compute a position of the ultrasound sensor of the interventional device relative to the ultrasound field based on ultrasound signals transmitted between the beamforming ultrasound imaging probe and the ultrasound sensor, and to provide an icon in the reconstructed ultrasound image based on the computed position of the ultrasound sensor.

16. The method according to claim 10, further comprising:
receiving signals indicative of detected interference on at least one of the first electrical conductor or the second electrical conductor; and
adjusting the capacitance based on the received signals.

17. The method according to claim 10, further comprising outputting a signal corresponding to an amplified difference between an electrical signal on the first electrical conductor and an electrical signal on the second electrical conductor.

18. The method according to claim 10, wherein the sensor is an ultrasound sensor; and the method further comprising:
communicating with an ultrasound imaging probe configured to generate an ultrasound field;
reconstructing an ultrasound image corresponding to the ultrasound field of the beamforming ultrasound imaging probe; and
computing a position of the ultrasound sensor of the interventional device relative to the ultrasound field based on ultrasound signals transmitted between the beamforming ultrasound imaging probe and the ultrasound sensor, and to provide an icon in the reconstructed ultrasound image based on the computed position of the ultrasound sensor.

* * * * *